United States Patent
Ao et al.

(10) Patent No.: US 8,746,399 B2
(45) Date of Patent: Jun. 10, 2014

(54) ACOUSTIC WAVEGUIDE ASSEMBLIES

(71) Applicant: General Electric Company, Schenectady, NY (US)

(72) Inventors: Xiaolei Shirley Ao, Lexington, MA (US); Jin Chang Xu, Andover, MA (US); John Albert Umina, Waltham, MA (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 13/970,136

(22) Filed: Aug. 19, 2013

(65) Prior Publication Data

US 2013/0329930 A1 Dec. 12, 2013

Related U.S. Application Data

(62) Division of application No. 13/314,963, filed on Dec. 8, 2011, now Pat. No. 8,511,424.

(51) Int. Cl.
 *G10K 11/00* (2006.01)
(52) U.S. Cl.
 USPC .......................................................... 181/196

(58) Field of Classification Search
 USPC .......... 181/139, 196; 73/644, 861.18, 861.12, 73/861.23, 861.25
 See application file for complete search history.

(56) References Cited

U.S. PATENT DOCUMENTS

| | | | |
|---|---|---|---|
| 4,893,496 A | 1/1990 | Bau et al. | |
| 5,000,045 A * | 3/1991 | Secoy | 73/587 |
| 5,159,838 A | 11/1992 | Lynnworth | |
| 5,824,915 A | 10/1998 | Hujzer et al. | |
| 6,047,602 A | 4/2000 | Lynnworth | |
| 6,343,511 B1 | 2/2002 | Lynnworth et al. | |
| 6,876,128 B2 | 4/2005 | Nguyen | |
| 6,889,552 B2 | 5/2005 | Nguyen et al. | |
| 6,912,918 B1 * | 7/2005 | Lynnworth et al. | 73/861.26 |
| 7,086,286 B1 | 8/2006 | McCarey, Jr. et al. | |
| 2003/0051558 A1 | 3/2003 | Melnikov et al. | |
| 2009/0007694 A1 | 1/2009 | Breeuwer | |
| 2009/0016555 A1 | 1/2009 | Lynnworth | |

* cited by examiner

*Primary Examiner* — Jeremy Luks
(74) *Attorney, Agent, or Firm* — Hiscock & Barclay LLP (57) ABSTRACT

Acoustic waveguides are disclosed for mounting to a conduit. The acoustic waveguides provide a mounting area that minimizes the effect of the mount on the acoustic wave traveling through the waveguide while providing an effective seal, even under high pressure conditions.

16 Claims, 9 Drawing Sheets

ACOUSTIC WAVEGUIDE ASSEMBLIES

CROSS-REFERENCE TO RELATED APPLICATIONS

This application is a divisional of U.S. patent application Ser. No. 13/314,963, filed Dec. 8, 2011 and entitled Acoustic Waveguide Assemblies, now U.S. Pat. No. 8,511,424, the entirety of which is incorporated herein by reference.

BACKGROUND OF THE INVENTION

The subject matter disclosed herein relates to acoustic waveguide assemblies for mounting an acoustic waveguide to a conduit.

Acoustic waveguides can be used to measure the characteristics (e.g., density, viscosity, level, temperature, etc.) of a fluid traveling in a conduit using acoustic waves. In a typical acoustic waveguide, a transducer assembly launches an acoustic wave into a waveguide that is mounted and sealed to the conduit and inserted into the fluid. The time of flight of the acoustic wave in the section of the waveguide inserted into the fluid is a function of the characteristics of the fluid and therefore can be used to determine those characteristics.

Some acoustic wave types require that the waveguide be a thin elongated rod. One of the limitations of these thin elongated rods that prevent use in most commercial and industrial applications, especially in high pressure installations, is the difficulty of mounting and sealing the waveguide to the conduit in a way that will not significantly affect the acoustic wave as it passes through the waveguide in the area of the seal. Sealing with an o-ring around the thin elongated rod of the waveguide is also difficult, especially in high pressure installations. While seals made of polytetrafluoroethylene (PTFE) have been used in laboratory settings, those seals are not sufficient for long term use under high pressure as the seals can deform over time and fail.

The discussion above is merely provided for general background information and is not intended to be used as an aid in determining the scope of the claimed subject matter.

BRIEF DESCRIPTION OF THE INVENTION

Acoustic waveguide assemblies are disclosed for mounting an acoustic waveguide to a conduit. The acoustic waveguide assemblies provide a mounting area that minimizes the effect of the mount on the acoustic wave traveling through the acoustic waveguide while providing an effective seal, even under high pressure conditions. An advantage that may be realized in the practice of some disclosed embodiments of the acoustic waveguides is allowing the use of thin elongated waveguides for more accurate density measurements that can provide more accurate flow measurements.

In one exemplary embodiment, an acoustic waveguide assembly for mounting to a conduit is disclosed. The acoustic waveguide comprises a waveguide rod having a proximal end and a distal end, a waveguide sensor connected to the distal end of the waveguide rod, and a disk coupler circumferentially surrounding a portion of the waveguide rod, wherein the disk coupler provides a surface to mount the waveguide rod to the conduit.

In another exemplary embodiment, the acoustic waveguide comprises a waveguide rod having a proximal end and a distal end, a waveguide sensor connected to the distal end of the waveguide rod, and a disk coupler circumferentially surrounding a portion of the waveguide rod, wherein the disk coupler provides a surface to mount the waveguide rod to the conduit. A transducer assembly comprising at least two portions is coupled to the waveguide rod at the proximal end.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which.

DETAILED DESCRIPTION OF THE INVENTION

Figure 1:
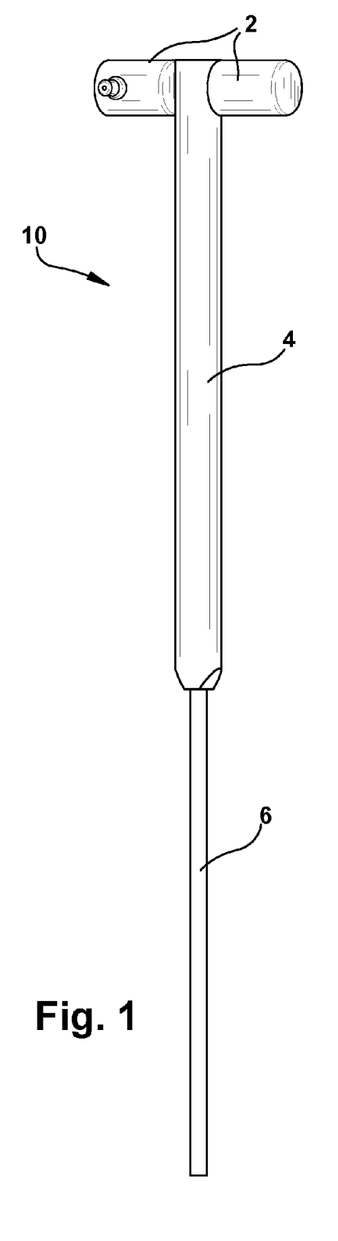
FIG. 1 is perspective view of an exemplary acoustic waveguide.

FIG. 1 is a perspective view of an exemplary acoustic waveguide 10. In one embodiment, a transducer assembly 2 is coupled to the proximal end of a waveguide rod 4. The distal end of the waveguide rod 4 can connect to a waveguide sensor 6, which is the portion of the acoustic waveguide 10 that will be submerged in the fluid. The transducer assembly 2 can comprise two transducers on opposite sides of the waveguide rod 4 and be configured to launch an acoustic wave into the acoustic waveguide 10. Each of the transducers can comprise a piezoelectric crystal encapsulated by packaging, or in another embodiment, only comprise the piezoelectric crystal.

In different embodiments, the mounting locations of the transducers on the waveguide rod 4, mounting angles of the transducers with respect to the longitudinal axis of the waveguide rod 4, polarity of the transducers, and the excitation pulse received by the transducers can be modified to launch particular acoustic waves (e.g., ultrasonic torsional, extensional, flexural waves) into the waveguide rod 4. Although the exemplary acoustic waveguides disclosed herein will be described with respect to use with torsional waves, it will be understood that the waveguides can be used for different acoustic waves.

An ultrasonic torsional wave is a wave motion in which the vibrations of the medium are periodic twisting motions around the direction of propagation along the azimuthal direction of the torsional waveguide. For use with torsional waves, the waveguide rod 4 can be a thin (e.g., 0.25 in. diameter (6.35 mm) for a 100 kHz wave, 0.375 in. diameter (9.53 mm) for a 75 kHz wave, 0.50 in. diameter (12.70 mm) for a 50 kHz wave), elongated rod having a circular cross-section into which the transducer assembly 2 launches the ultrasonic torsional wave. The waveguide sensor 6 can be a thin, elongated non-circular cross-section (e.g., diamond shaped), which is submerged in the fluid. When the ultrasonic torsional wave traveling down the waveguide rod 4 hits the interface between the waveguide rod 4 and the waveguide sensor 6, the ultrasonic torsional wave is partially reflected at the interface back to the transducer assembly 2 providing a first time of flight measurement, while the remainder of the ultrasonic torsional wave will transmit through the waveguide sensor 6. When the remainder of the ultrasonic torsional wave hits the end of the waveguide sensor 6, the ultrasonic torsional wave will reflect back to the transducer assembly 2, providing a second time of flight measurement. The time of flight in the waveguide sensor 6 depends, in part, upon the density of the fluid, with a slower time of flight for more dense fluids and a faster time of flight for less dense fluids. The slow speed of the ultrasonic torsional wave in the waveguide sensor 6 provides high sensitivity to changes in the density of the fluid surrounding that section of the acoustic waveguide 10. Knowledge of the actual density of a fluid, along with traditional transit time or Doppler measurements that can only provide flow velocity, can provide more accurate mass flow measurements than measurements using a calculated density based on temperature and pressure of the fluid.

Figure 2:
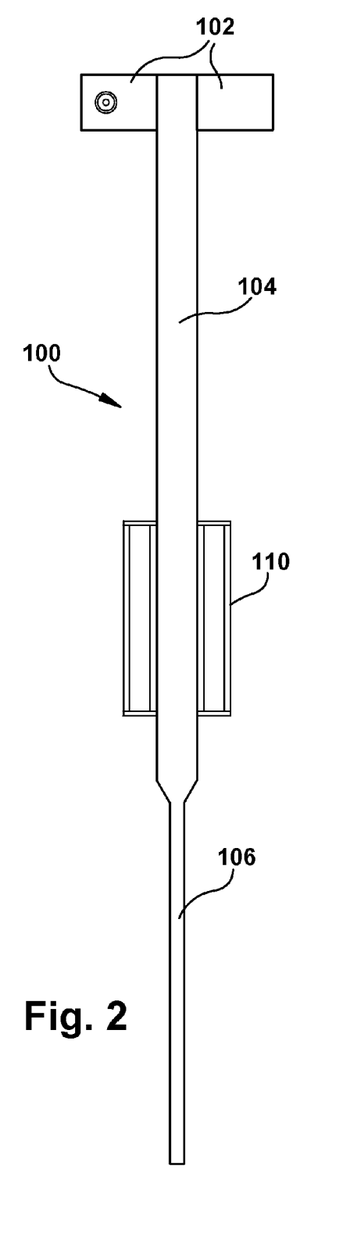
FIG. 2 is a cross-section of another exemplary acoustic waveguide with a tube coupler for mounting the acoustic waveguide to a conduit.
Figure 3:
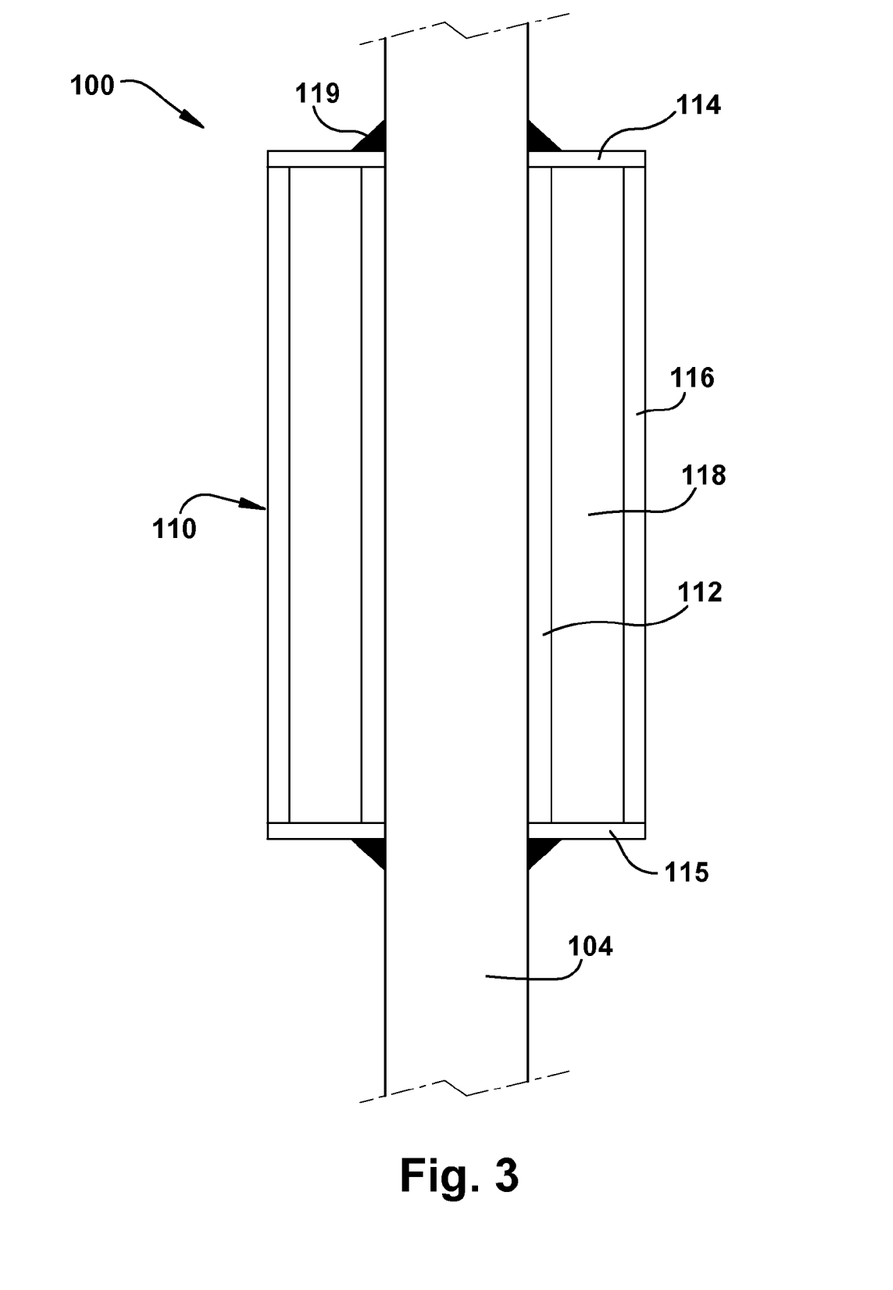
FIG. 3 is a cross-section of the portion of the exemplary acoustic waveguide of FIG. 2 showing the tube coupler.
Figure 4:
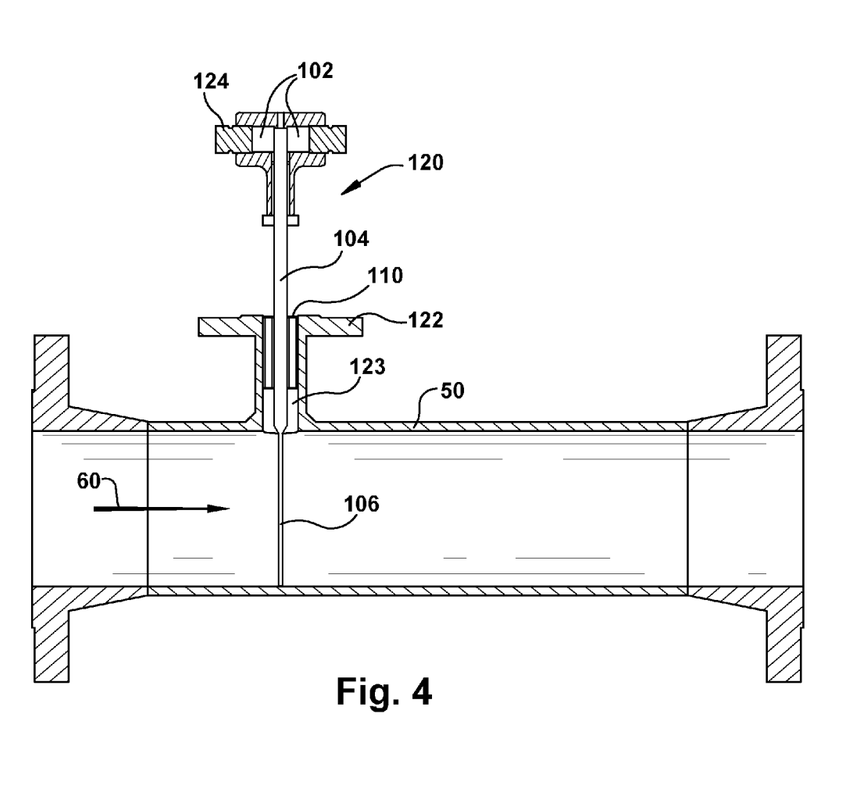
FIG. 4 is a cross-section of an exemplary acoustic waveguide assembly for mounting the acoustic waveguide of FIG. 2 to a conduit through a nozzle.
Figure 5:
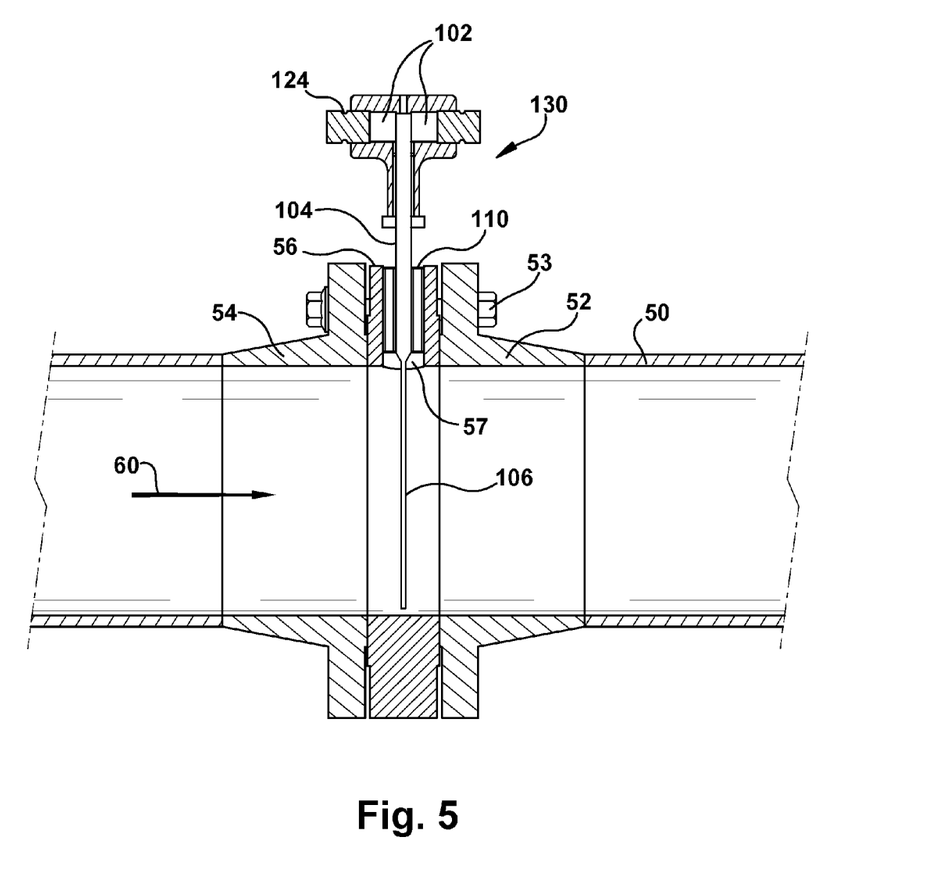
FIG. 5 is a cross-section of another exemplary acoustic waveguide assembly for mounting the acoustic waveguide of FIG. 2 to a conduit in a middle flange.
Figure 6:
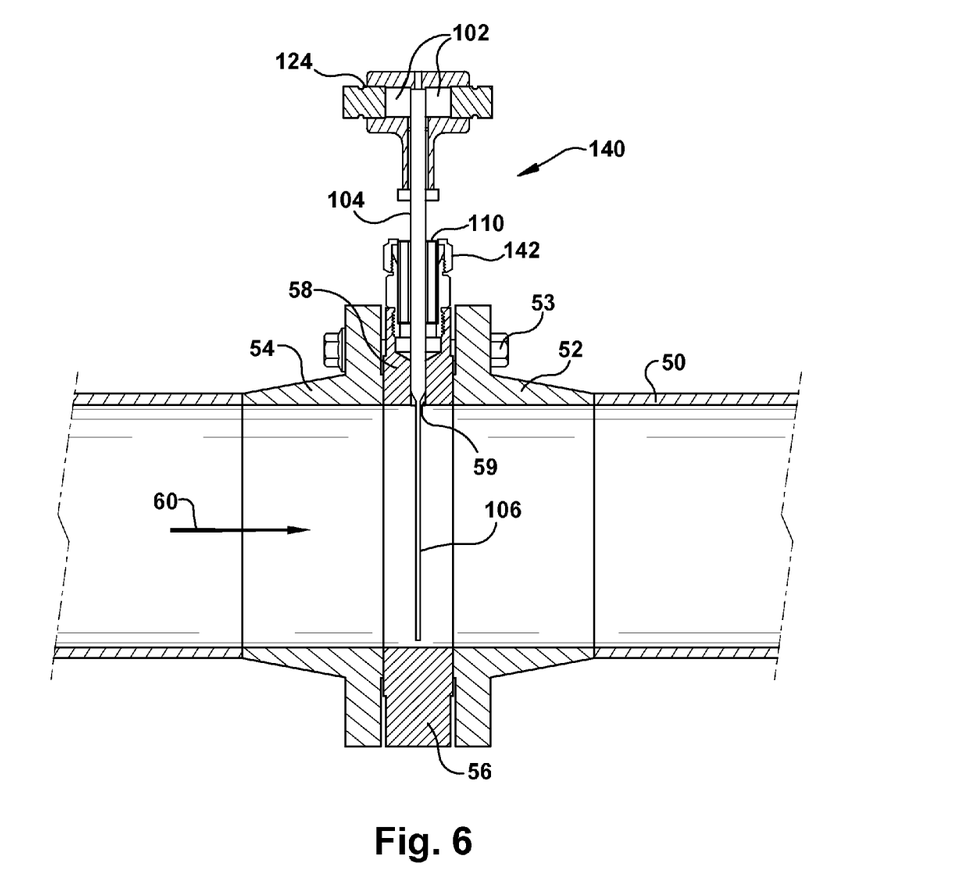
FIG. 6 is a cross-section of yet another exemplary acoustic waveguide assembly for mounting the acoustic waveguide of FIG. 2 to a conduit using a compression fitting in a flange.

FIG. 2 is another exemplary acoustic waveguide 100 with a tube coupler 110 for mounting the acoustic waveguide 100 to a conduit 50 (see FIGS. 4, 5, and 6). Although the figures show the exemplary acoustic waveguides mounted to a pipe, it will be understood that the acoustic waveguides can be mounted to a variety of conduits in which fluid travels (e.g., a pipe, tube, vessel, tank, etc.). FIG. 3 is a cross-section of a portion of the exemplary acoustic waveguide 100 of FIG. 2 showing the tube coupler 110. In one embodiment, a transducer assembly 102 is coupled to the proximal end of the waveguide rod 104, which can have a circular cross-section. The distal end of the waveguide rod 104 can connect to a waveguide sensor 106, which is the portion of the acoustic waveguide 100 that will be submerged in the fluid and can have a non-circular cross-section.

The tube coupler 110 circumferentially surrounds a portion of the waveguide rod 104 to provide a surface for mounting the acoustic waveguide 100 to a conduit 50. The exemplary tube coupler 110 comprises a first end 114 (e.g., a flat or curved disk) circumferentially surrounding the waveguide rod 104 at a first location and a second end 115 (e.g., a flat or curved disk) circumferentially surrounding the waveguide rod 104 at a second location. The tube coupler 110 also comprises an inner sleeve 112 circumferentially surrounding the waveguide rod 104 and extending from the first end 114 to the second end 115 proximate the waveguide rod 104. In one embodiment, the inner sleeve 112 is not fixedly attached to the waveguide rod 104 to minimize contact between the tube coupler 110 and the waveguide rod 104 to avoid dampening of the acoustic waves traveling through the waveguide rod 104. For example, the inner sleeve 112 can form a close sliding fit with the waveguide rod 104 without applying pressure on the waveguide rod 104. The inner sleeve 112 can be made of a material different than the waveguide rod 104 that has a different acoustic impedance than the waveguide rod 104 to provide acoustic isolation between the waveguide rod 104 and the tube coupler 110.

The tube coupler 110 can further comprise an outer tube 116 circumferentially surrounding the inner sleeve 112 and extending from the first end 114 to the second end 115, forming a cavity 118 between the inner sleeve 112 and the outer tube 116. The tube coupler 110 can have varying lengths to provide the desired acoustic performance of the acoustic waveguide 110. The cavity 118 can be filled with filler (e.g., a liquid or a non-metallic solid (e.g., epoxy)) that can provide mechanical support for the second end 115, which provides a boundary against the pressure in the conduit 50 (see FIGS. 4, 5, and 6). In addition to providing mechanical support, the filler can be chosen to provide acoustic isolation between the waveguide rod 104 and the tube coupler 110.

The first end 114 and the second end 115 of the tube coupler 110 can be relatively thin (e.g., 0.007 in. (0.178 mm) to 0.010 in. (0.254 mm). The first end 114 and second end 115 can be welded to the waveguide rod 104, while the inner sleeve 112 and the outer tube 116 can be welded to the first end 114 and the second end 115. The components of the tube coupler 110 may be made of corrosion resistant materials (e.g., stainless steel 316, titanium, graphite) and welded together using different welding techniques, including, e.g., groove welding, fillet welding, resistance welding, e-beam welding, friction welding, or brazing.

FIG. 4 is a cross-section of an exemplary acoustic waveguide assembly 120 for mounting the acoustic waveguide 100 of FIG. 2 to a conduit 50 through a nozzle 122. The transducer assembly 102 can be mounted to the waveguide rod 104 using a clamp 124 (e.g., a T-clamp). The clamp 124 can be spring loaded to provide the necessary contact pressure between the transducer assembly 102 and the waveguide rod 104 to ensure proper transmission of the acoustic wave into the waveguide rod 104. A nozzle 122 provides a port 123 for accessing the fluid inside of the conduit 50. Although the nozzle 122 and the port 123 are shown to be oriented perpendicular to the conduit 50 and the direction of flow 60 of the fluid in FIG. 4, it will be understood that the orientation can be at different angles or locations on the conduit 50 (e.g., horizontal, vertical, elbow, angled). The tube coupler 110 can be inserted into the port 123 of the nozzle 122 such that the waveguide sensor 106 extends into the fluid flowing in the conduit 50. The length of the waveguide sensor 106 can be the same as the inner diameter of the conduit 50, recessed in the port 123 of the nozzle 122, or mounted flush with the inner diameter of the conduit 50. As shown in FIG. 4, the tube coupler 110 forms a seal of the port 123 of the nozzle 122 and therefore must withstand the pressure in the conduit 50. The second end 115 and the filler in the cavity 118 (see FIG. 3) of the tube coupler 110 provide the mechanical support to withstand the pressure in the conduit 50. In addition, an o-ring (not shown) can be installed in the port 123 of the nozzle 122 proximate the outer tube 116 of the tube coupler 110 (see FIG. 3) to further seal the port 123. The tube coupler 110 can be fixedly attached to the port 123 of the nozzle 122 by, e.g., welding or threading.

FIG. 5 is a cross-section of another exemplary acoustic waveguide assembly 130 for mounting the acoustic waveguide 100 of FIG. 2 to a conduit 50 in a flange. A first section of the conduit 50 terminating in a first flange 52 is coupled to a second section of the conduit 50 terminating in a second flange 54 through a middle flange 56 by a plurality of bolts 53 extending through the first flange 52, the second flange 54, and the middle flange 56. The middle flange 56 provides a port 57 for accessing the fluid inside of the conduit 50. The tube coupler 110 can be inserted into the port 57 of the middle flange 56 such that the waveguide sensor 106 extends into the fluid flowing in the conduit 50. As shown in FIG. 5, the tube coupler 110 forms a seal of the port 57 of the middle flange 56 and therefore must withstand the pressure in the conduit 50. In addition, an o-ring (not shown) can be installed in the port 57 of the middle flange 56 proximate the outer tube 116 of the tube coupler 110 (see FIG. 3) to further seal the port 57.

FIG. 6 is a cross-section of yet another exemplary acoustic waveguide assembly 140 for mounting the acoustic waveguide 100 of FIG. 2 to a conduit 50 using a compression fitting 142 in a flange. A first section of the conduit 50 terminating in a first flange 52 is coupled to a second section of the conduit 50 terminating in a second flange 54 through a middle flange 58 by a plurality of bolts 53 extending through the first flange 52, the second flange 54, and the middle flange 58. The middle flange 58 provides a port 59 for accessing the fluid inside of the conduit 50. The tube coupler 110 can be inserted into a compression fitting 142, which is then inserted into the port 59 of the middle flange 58 such that the waveguide sensor 106 extends into the fluid flowing in the conduit 50. The port 59 of the middle flange 58 can be shaped to receive the compression fitting 142 (e.g., threaded to receive the threads of the compression fitting 142). As shown in FIG. 6, the tube coupler 110 forms a seal of the port 59 of the middle flange 58 and therefore must withstand the pressure in the conduit 50.

Figure 7:
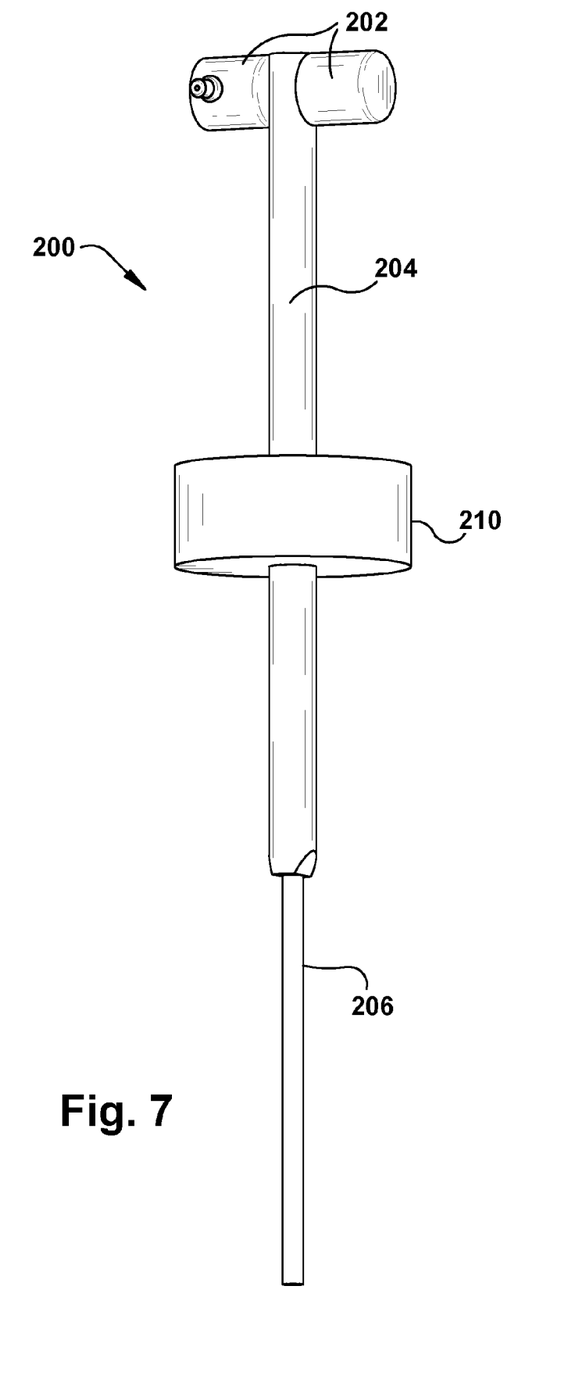
FIG. 7 is a perspective view of yet another exemplary acoustic waveguide with a disk coupler for mounting the acoustic waveguide to a conduit.
Figure 8:
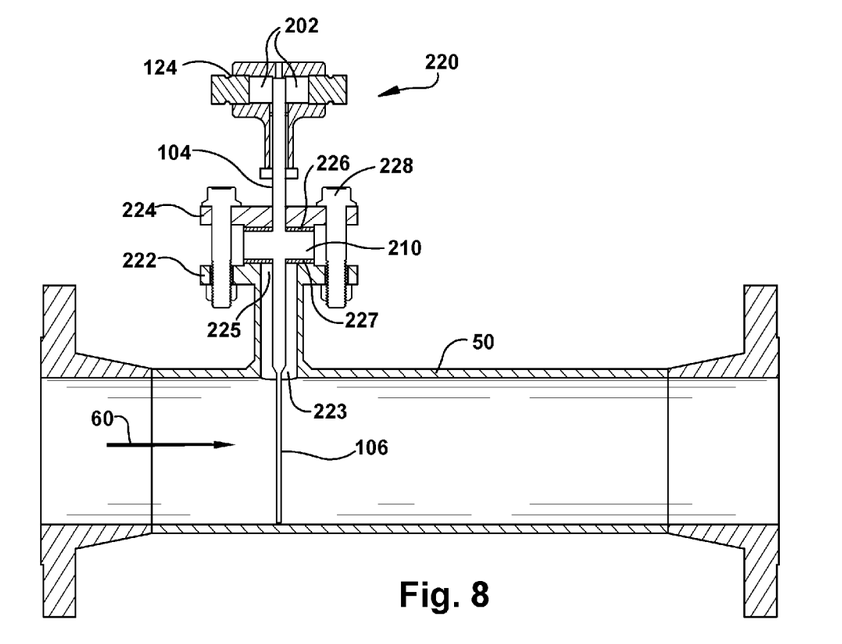
FIG. 8 is a cross-section of an exemplary acoustic waveguide assembly for mounting the acoustic waveguide of FIG. 7 to a conduit through a nozzle.

FIG. 7 is a perspective view of yet another exemplary acoustic waveguide 200 with a disk coupler 210 for mounting the acoustic waveguide 200 to a conduit 50 (see FIG. 8). In one embodiment, a transducer assembly 202 is coupled to the proximal end of the waveguide rod 204, which can have a circular cross-section. The distal end of the waveguide rod 204 can connect to a waveguide sensor 206, which is the portion of the acoustic waveguide 200 that will be submerged in the fluid and can have a non-circular cross-section. The disk coupler 210 circumferentially surrounds a portion of the waveguide rod 204 to provide a surface for mounting the acoustic waveguide 200 to a conduit 50. In one embodiment, the disk coupler 210 can be welded to the waveguide rod 204, while in another embodiment, the disk coupler 210 can be integral with the waveguide rod 204 if both are made by machining the same block of material.

FIG. 8 is a cross-section of an exemplary acoustic waveguide assembly 220 for mounting the acoustic waveguide 200 of FIG. 7 to a conduit 50 through a nozzle 222. The transducer assembly 202 can be mounted to the waveguide rod 204 using a clamp 124 (e.g., a T-clamp). The clamp 124 can be spring loaded to provide the necessary contact pressure between the transducer assembly 202 and the waveguide rod 204 to ensure proper transmission of the acoustic wave into the waveguide rod 204. A nozzle 222 provides a port 223 for accessing the fluid inside of the conduit 50. Although the nozzle 222 and the port 223 are shown to be oriented perpendicular to the conduit 50 and the direction of flow 60 of the fluid in FIG. 8, it will be understood that the orientation can beat different angles or locations on the conduit 50 (e.g., horizontal, vertical, elbow, angled). The bottom side of disk coupler 210 can be mounted on the outlet 225 of the port 223 of the nozzle 222 such that the waveguide sensor 206 extends through the port 223 into the fluid flowing in the conduit 50. The disk coupler 210 is mounted between a top flange 224 on the top side of the disk coupler 210 and the nozzle 222 with a plurality of bolts 228 extending through the top flange 224 and the nozzle 222. As shown in FIG. 8, the disk coupler 210 forms a seal of the port 223 of the nozzle 222. In addition, a first gasket 226 can be installed between the top surface of the disk coupler 210 and the top flange 224. A second gasket 227 can be installed between the bottom surface of the disk coupler 210 and the outlet 225 of the port 223 of the nozzle 222 to further seal the port 223.

Figure 9:
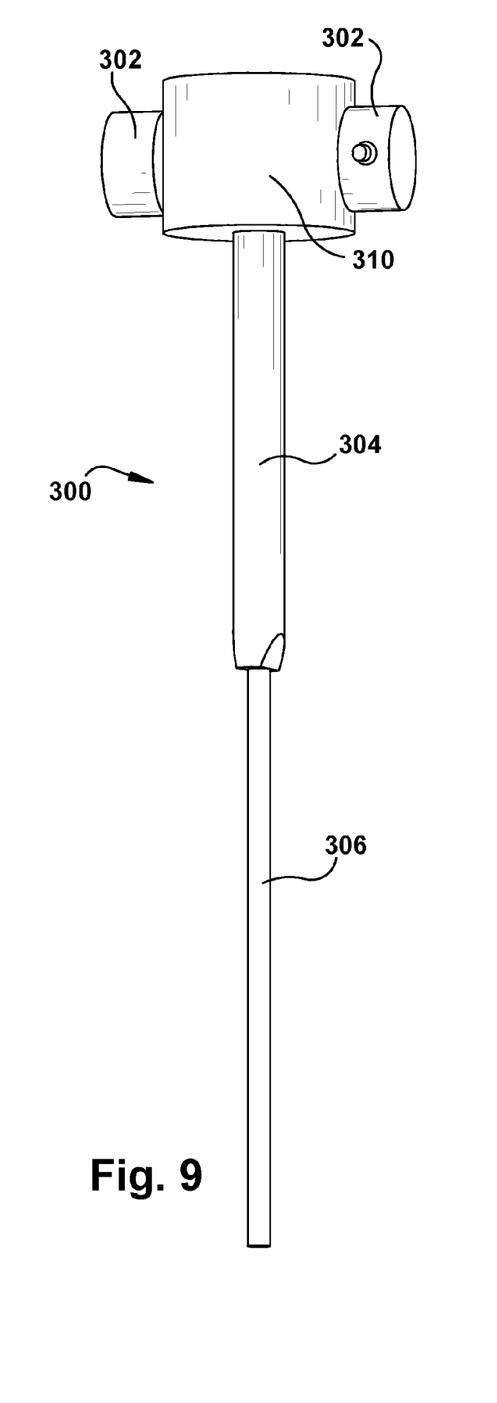
FIG. 9 is a perspective view of still another exemplary acoustic waveguide with a disk coupler for mounting the acoustic waveguide to a conduit.
Figure 10:
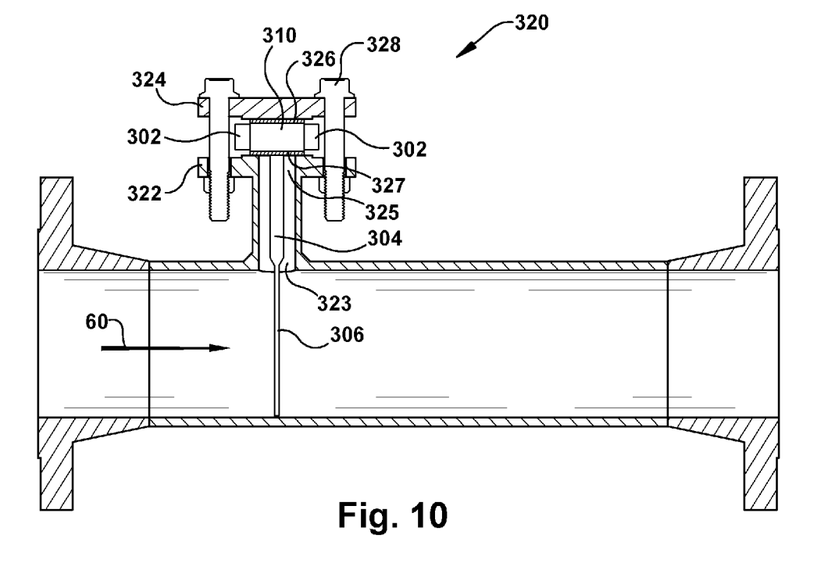
FIG. 10 is a cross-section of an exemplary acoustic waveguide assembly for mounting the acoustic waveguide of FIG. 9 to a conduit through a nozzle.

FIG. 9 is a perspective view of still another exemplary acoustic waveguide 300 with a disk coupler 310 for mounting the acoustic waveguide 300 to a conduit 50 (see FIG. 10). The distal end of the waveguide rod 304 can connect to a waveguide sensor 306, which is the portion of the acoustic waveguide 300 that will be submerged in the fluid and can have a non-circular cross-section. The disk coupler 310 circumferentially surrounds a portion of the waveguide rod 304 to provide a surface for mounting the acoustic waveguide 300 to a conduit 50. In one embodiment, the disk coupler 310 can be welded to the waveguide rod 304, while in another embodiment, the disk coupler 310 can be integral with the waveguide rod 304 if both are made by machining the same block of material. In still another embodiment, the disk coupler 310 can be coupled to the waveguide rod 304 using mating threads on each part.

As shown in FIG. 9, the transducer assembly 302 is coupled to the circumference of the disk coupler 310. The transducer assembly 302 can be coupled to the disk coupler 310 using, e.g., an adhesive (epoxy) or a circumferential clamp. The transducer assembly 302 can comprise two transducers on opposite sides of the disk coupler 310 and be configured to launch an acoustic wave into the acoustic waveguide 300. Each of the transducers can comprise a piezoelectric crystal encapsulated by packaging, or in another embodiment, only comprise the piezoelectric crystal.

FIG. 10 is a cross-section of an exemplary acoustic waveguide assembly 320 for mounting the acoustic waveguide 300 of FIG. 9 to a conduit 50 through a nozzle 322. The transducer assembly 302 can be coupled to the disk coupler 310 to ensure proper transmission of the acoustic wave into the waveguide rod 304. Coupling the transducer assembly 302 to the disk coupler 310 eliminates the need for a transducer clamp and can minimize the amount of acoustic signal lost through the disk coupler 310. A nozzle 322 provides a port 323 for accessing the fluid inside of the conduit 50. Although the nozzle 322 and the port 323 are shown to be oriented perpendicular to the conduit 50 and the direction of flow 60 of the fluid in FIG. 10, it will be understood that the orientation can beat different angles or locations on the conduit 50 (e.g., horizontal, vertical, elbow, angled). The disk coupler 310 can be mounted on the outlet 325 of the port 323 of the nozzle 322 such that the waveguide sensor 306 extends through the port 323 into the fluid flowing in the conduit 50. The disk coupler 310 is mounted between a top flange 324 resting on top of the disk coupler 310 and the nozzle 322 with a plurality of bolts 328 extending through the top flange 324 and the nozzle 322. As shown in FIG. 10, the disk coupler 210 forms a seal of the port 323 of the nozzle 322. In addition, a first gasket 326 can be installed between the top surface of the disk coupler 310 and the top flange 324. A second gasket 327 can be installed between the bottom surface of the disk coupler 310 and the outlet 325 of the port 323 of the nozzle 322 to further seal the port 323.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. An acoustic waveguide assembly for mounting to a conduit, the acoustic waveguide assembly comprising:
   an acoustic waveguide comprising a waveguide rod having a proximal end and a distal end;
   a waveguide sensor connected to the distal end of the waveguide rod;
   a disk coupler circumferentially surrounding a portion of the waveguide rod, wherein the disk coupler provides a first side and a second side to mount the waveguide rod to the conduit;
   a nozzle on the first side of the disk coupler;
   a flange on the second side of the disk coupler, opposite the first side; and
   a plurality of bolts extending through the flange and through the nozzle to secure the disk coupler therebetween.

2. The acoustic waveguide assembly of claim 1, wherein the nozzle comprises a port for accessing the inside of the conduit, and wherein the first side of the disk coupler is mounted on an outlet of the port of the nozzle such that the waveguide sensor extends through the port and into the conduit.

3. The acoustic waveguide assembly of claim 1, further comprising a transducer assembly coupled to the proximal end of the waveguide rod.

4. The acoustic waveguide assembly of claim 1, wherein the disk coupler is located at the proximal end of the waveguide rod.

5. The acoustic waveguide assembly of claim 4, further comprising a transducer assembly coupled to the disk coupler.

6. The acoustic waveguide assembly of claim 1, wherein the waveguide rod has a circular cross-section.

7. The acoustic waveguide assembly of claim 1, wherein the waveguide sensor has a non-circular cross-section.

8. The acoustic waveguide assembly of claim 1, wherein the disk coupler is welded to the waveguide rod.

9. The acoustic waveguide assembly of claim 1, wherein the disk coupler is integrally formed with the waveguide rod.

10. The acoustic waveguide assembly of claim 9, wherein the waveguide rod and the disk coupler are formed from the same block of material.

11. An acoustic waveguide assembly for mounting to a conduit, the acoustic waveguide assembly comprising:
    an acoustic waveguide comprising a waveguide rod having a proximal end and a distal end;
    a waveguide sensor connected to the distal end of the waveguide rod;
    a disk coupler circumferentially surrounding a portion of the waveguide rod, wherein the disk coupler provides a first side and a second side to mount the waveguide rod to the conduit;
    a nozzle on the first side of the disk coupler;
    a flange on the second side of the disk coupler, opposite the first side;
    a plurality of bolts extending through the flange and through the nozzle to secure the disk coupler therebetween; and
    a transducer assembly comprising at least two portions coupled to the waveguide rod at the proximal end.

12. The acoustic waveguide assembly of claim 11, wherein the portions of the transducer assembly are coupled to an outside surface of the waveguide rod, and wherein the portions of the transducer assembly are disposed on opposing sides of the waveguide rod.

13. The acoustic waveguide assembly of claim 12, wherein the transducer assembly is acoustically coupled to the waveguide rod via contact pressure by the portions of the transducer assembly against the opposing sides of the waveguide rod.

14. The acoustic waveguide assembly of claim 13, further comprising a clamp pressing against the portions of the transducer assembly to provide the contact pressure.

15. The acoustic waveguide assembly of claim 14, wherein the clamp comprises a spring loaded clamp.

16. An acoustic waveguide assembly for mounting to a conduit, the acoustic waveguide assembly comprising:
    an acoustic waveguide comprising a waveguide rod having a proximal end and a distal end, a waveguide sensor connected to the distal end of the waveguide rod, and a disk coupler circumferentially surrounding a portion of the waveguide rod, wherein the disk coupler provides a surface to mount the waveguide rod to the conduit;
    a transducer assembly comprising at least two portions coupled to the waveguide rod at the proximal end; and
    a clamp pressing against the portions of the transducer assembly to acoustically couple the transducer assembly to the waveguide rod via contact pressure by the portions of the transducer assembly against the waveguide rod,
    wherein the clamp comprises a spring loaded clamp, the portions of the transducer assembly are coupled to an outside surface of the waveguide rod, and wherein the portions of the transducer assembly are disposed on opposing sides of the waveguide rod.

* * * * *